(12) United States Patent
Wu et al.

(10) Patent No.: US 11,185,346 B1
(45) Date of Patent: Nov. 30, 2021

(54) MULTI-BLADE CUTTING DEVICE

(71) Applicant: MUSCULOSKELETAL TRANSPLANT FOUNDATION, Edison, NJ (US)

(72) Inventors: Kevin Wu, Morganville, NJ (US); Todd J. Nilsen, Howell, NJ (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 102 days.

(21) Appl. No.: 15/866,833

(22) Filed: Jan. 10, 2018

Related U.S. Application Data (60) Provisional application No. 62/444,653, filed on Jan. 10, 2017.

(51) Int. Cl.
| A61B 17/322 | (2006.01) |
| A61B 17/32 | (2006.01) |
| A61B 17/3211 | (2006.01) |
| A61B 17/14 | (2006.01) |
| A61B 18/00 | (2006.01) |

(52) U.S. Cl.
CPC ...... *A61B 17/322* (2013.01); *A61B 17/32002* (2013.01); *A61B 17/142* (2016.11); *A61B 17/3211* (2013.01); *A61B 2018/00601* (2013.01)

(58) Field of Classification Search
CPC ............ A61B 17/322; A61B 17/32002; A61B 2018/00601
See application file for complete search history.

(56) References Cited

U.S. PATENT DOCUMENTS

| 7,625,384 | B2 * | 12/2009 | Eriksson | A61B 17/322 |
| | | | | 606/132 |
| 10,537,349 | B1 | 1/2020 | Hayzlett et al. | |
| 2011/0077664 | A1 * | 3/2011 | Schulz | A61B 17/322 |
| | | | | 606/132 |
| 2014/0107668 | A1 * | 4/2014 | Zolotov | A61B 17/322 |
| | | | | 606/132 |
| 2015/0209220 | A1 * | 7/2015 | Lin | A61H 15/0092 |
| | | | | 601/119 |
| 2020/0113592 | A1 | 4/2020 | Hayzlett et al. | |

FOREIGN PATENT DOCUMENTS

CN 108247726 A 7/2018

OTHER PUBLICATIONS

U.S. Appl. No. 15/867,472, filed Jan. 10, 2018.

* cited by examiner

*Primary Examiner* — Sarah A Simpson
(74) *Attorney, Agent, or Firm* — Marcella M. Bodner; Cole Schotz, P.C.

(57) ABSTRACT

A cutting device is provided having multiple evenly-spaced cutting blades and which is useful for producing tissue forms comprising membranous tissue fragments which are relatively uniformly sized and shaped. The present invention also relates to methods for using the cutter device to quickly and efficiently produce such tissue forms which are useful as grafts and can be flowable and easily passable through a luer-slip tip syringe or needle.

13 Claims, 5 Drawing Sheets

FIG. 9

MULTI-BLADE CUTTING DEVICE

CROSS-REFERENCE TO RELATED APPLICATIONS

The present application claims the benefit of U.S. Provisional Application No. 62/444,653, filed Jan. 10, 2017, the entire disclosure of which is incorporated by reference herein.

FIELD OF THE INVENTION

The present invention relates generally to a cutting device having multiple evenly-spaced cutting blades and which is useful for producing tissue forms comprising membranous tissue fragments. The present invention also relates to methods for using the cutter device to produce such tissue forms which are useful as grafts.

BACKGROUND OF THE INVENTION

Membranous tissues can be processed into tissue forms that are suitable for use as grafts in various surgical and medical procedures, including without limitation ophthalmological, orthopaedic, genitourinary, general surgery, cardiothoracic, wound healing, burn care, surgical anti-adhesion, and dental procedures. Membranous tissues are generally sheet like and, therefore, capable of being laid flat. Various membranous tissues exist including, without limitation, amnion, chorion, umbilical cord, fascia, submucosa, dermis, intestinal, pericardium, peritoneum, and many others.

The size, shape and consistency of the tissue forms often determine how the tissue forms may be applied and retained at surgical sites amenable to treatment with such grafts. Tissue forms which can be applied with a luer-slip tip syringe or needle may be useful for certain surgical sites that are relatively small or not readily accessible. Such tissue forms include those comprising small tissue fragments, or particles, having relatively uniform size and shape and which are derived from membranous tissue. A method for quickly and efficiently producing such fragmented membranous tissue forms from membranous tissues would also be useful.

Accordingly, it would be useful to develop devices capable of processing membranous tissues to produce tissue forms comprising small membranous tissue fragments, or particles, having relatively uniform size and shape. It would also be useful to develop methods of using such devices to produce such tissue forms quickly and efficiently, while retaining as much of the viable cell population and extracellular matrix structure as possible.

SUMMARY OF THE INVENTION

The present invention relates generally to a multi-blade cutting device for quickly and efficiently producing a tissue form comprising membranous tissue fragments derived from membranous tissue, as well as a method for using the cutting device to produce such tissue forms.

The present invention relates to a cutting device for producing a tissue form comprising uniformly sized and shaped membranous tissue fragments derived from membranous tissue, the device comprising:

a plurality of cutting blades, each having a size, a shape, a tapered cutting edge, a blade opening therethough, and a first distance between the blade opening and the cutting edge, wherein the size, the shape and the first distance are, respectively, the same for each of the plurality of cutting blades;

a plurality of spacer elements, each having a size, a shape, a thickness, a tissue facing edge, a spacer opening therethrough, and a second distance between the spacer opening and the tissue-facing edge, wherein the size, the shape, the thickness and the second distance are, respectively, the same for each of the plurality of spacer elements; and an elongated shaft for supporting and aligning the cutting blades and the spacer elements.

Furthermore, each of the plurality of cutting blades and each of the plurality of spacer elements are disposed on the elongated shaft, in side-by-side and alternating arrangement with one another, such that a respective one of the plurality of spacer elements is positioned between each respective pair of adjacent cutting blades and such that adjacent cutting blades are evenly spaced apart by a third distance which is equal to the thickness of the spacer elements; the blade openings and the spacer openings are all sized, shaped and positioned on their respective cutting blades and spacer elements such that the blade openings and spacer openings are aligned with one another and receive the elongated shaft therethrough; and the second distance of each of the plurality of spacer elements is less than the first distance of each of the plurality of cutting blades so that the tapered cutting edges of the cutting blades will cut entirely through a membranous tissue without obstruction or interference from the tissue-facing edge of the spacer elements when the cutting device is operated.

In some embodiments, the cutting device may also include a handle element sized and shaped to contain at least a portion of the elongated shaft and be manually held by a user during operation of the cutting device, and a guard element sized and shaped to cover at least a portion of the side-by-side and alternating cutting blades that is proximate a user during operation of the cutting device.

In an exemplary embodiment, the cutting device is a rotary cutter wherein the elongated shaft is a cylindrical shaft, which having a longitudinal rotational axis, the cutting blades are circular cutting blades, and the spacer elements are spacer disks, the blade openings are each centrally positioned on their respective circular cutting blade, the spacer openings are each centrally positioned on their respective spacer disks, and the circular cutting blades and the spacer disks are rotatably disposed on the cylindrical shaft.

The present invention also relates generally to a method for producing a tissue form comprising membranous tissue fragments from a membranous tissue using a cutting device having a plurality of cutting blades evenly spaced apart by a distance equal to a desired length or width of the membranous tissue fragments. The method involves the steps of: providing a membranous tissue; positioning the cutting device proximate to the membranous tissue; applying the cutting device in a first direction to the membranous tissue to form a first cut entirely through the membranous tissue and thereby create at least one strip in the membranous tissue; repositioning the cutting device, the membranous tissue, or both; and applying the cutting device in a second direction, which is different from the first direction, to form a second cut entirely through the membranous tissue and across the at least one strip which was formed by the step of applying the cutting device in the first direction, thereby producing uniformly sized and shaped membranous tissue fragments. In some embodiments, the method is performed using the cutting device described above.

BRIEF DESCRIPTION OF THE DRAWINGS

The present invention will be further explained with reference to the attached drawings, wherein.

DETAILED DESCRIPTION OF THE INVENTION

Detailed embodiments of the present invention are disclosed herein. It should be understood that the disclosed embodiments are merely illustrative of the invention that may be embodied in various forms. In addition, each of the examples given in connection with the various embodiments of the invention is intended to be illustrative, and not restrictive. It should be understood that although an exemplary embodiment of the present invention is described below as being a rotary cutting device having circular cutting blades, the cutting device may have other equally suitable and effective configurations and components.

As will be described in further detail below, a cutting device is provided for producing tissue forms from membranous tissue. The tissue forms produced are useful as grafts and comprise membranous tissue fragments having relatively uniform size and shape. Membranous tissue fragments are derived from membranous tissue. Such tissue forms are capable of being applied or implanted at surgical sites amenable to such treatment with a luer-slip tip syringe or needle.

In one exemplary embodiment, the cutting device has a plurality of cutting blades which are evenly spaced apart using spacer elements positioned in between each pair of cutting blades and each having a thickness equal to the distance between the cutting blades. The method generally involves applying force to the cutting device to cut a portion of an uncut processed membranous tissue in one direction to form strips. The uncut processed membranous tissue is then rotated from about 15 to about 165 degrees, such as for example without limitation about 90 degrees, and force is applied to the cutting device again to cut across the strips to form quadrilateral membranous tissue fragments, or particles of the tissue form.

The resulting relatively uniformly sized and shaped membranous tissue fragments are collected and may, themselves, provide the tissue form useful as a graft. The collected membranous tissue fragments may be stored in either a dried or wet state. Alternatively, and is often the case, the resulting relatively uniformly sized and shaped membranous tissue fragments may be combined with a liquid, such as cryopreservation solution, growth media, or storage media to provide the tissue form useful as a graft. Additionally, portions of the tissue form comprising relatively uniformly sized and shaped membranous tissue fragments may be separated or collected in desired quantities and placed into containers that are then sealed into packages. When the tissue fragments are combined with at least cryopreservation solution, the resulting tissue form may be cryopreserved, either before or after being placed into containers and sealed packages.

Cutting Device

Generally, the cutting device has a plurality of cutting blades that are arranged in a manner that will form straight evenly-spaced cuts in a membranous tissue, such as without limitation, with the cutting blades being parallel. The size of the spacing between the cutting blades and the angle of the second cut determines the width and length, as well as the overall shape, of the membranous tissue fragments.

The cutting device may be any of several different configurations, as will be readily recognized by persons of ordinary skill in the relevant art. It is understood that while a particular rotary configuration for the cutting device will now be described in detail, alternate configurations are possible.

Figure 1:
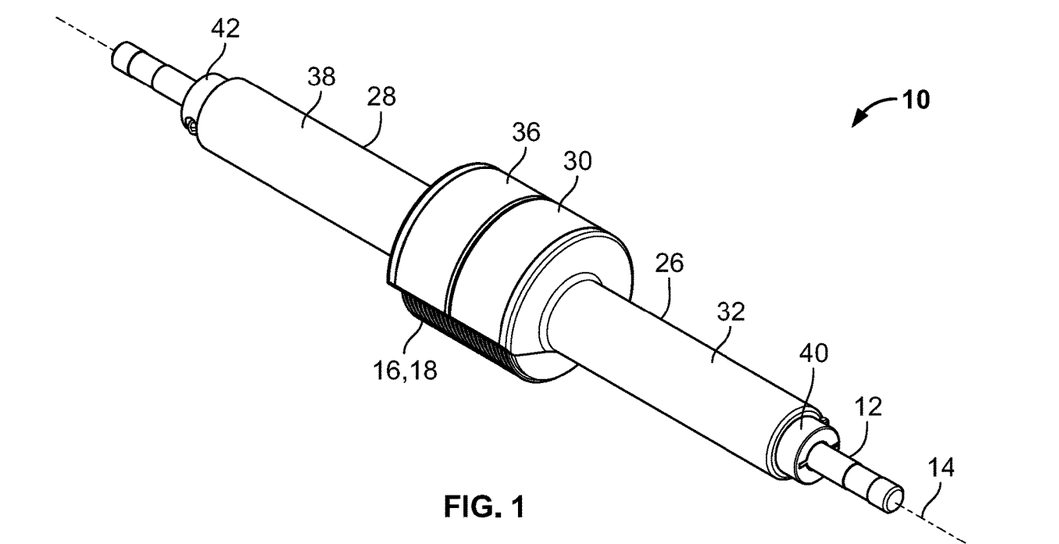
FIG. 1 is a perspective view of an exemplary embodiment of an assembled rotary cutter useful for producing the mini sheet tissue form described herein.
Figure 2:
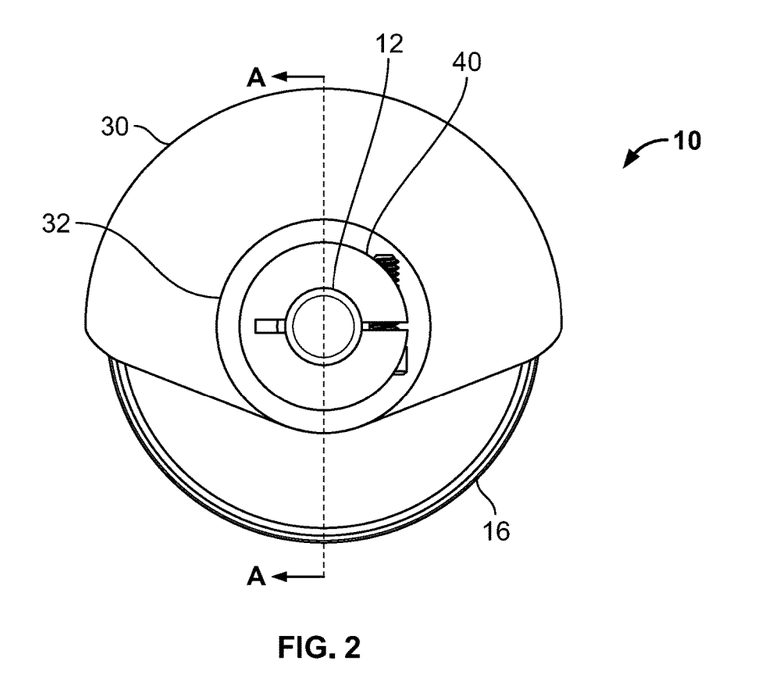
FIG. 2 is a plan view of the right side of the assembled rotary cutter of FIG. 1, of which the left side is a mirror image.
Figure 3:
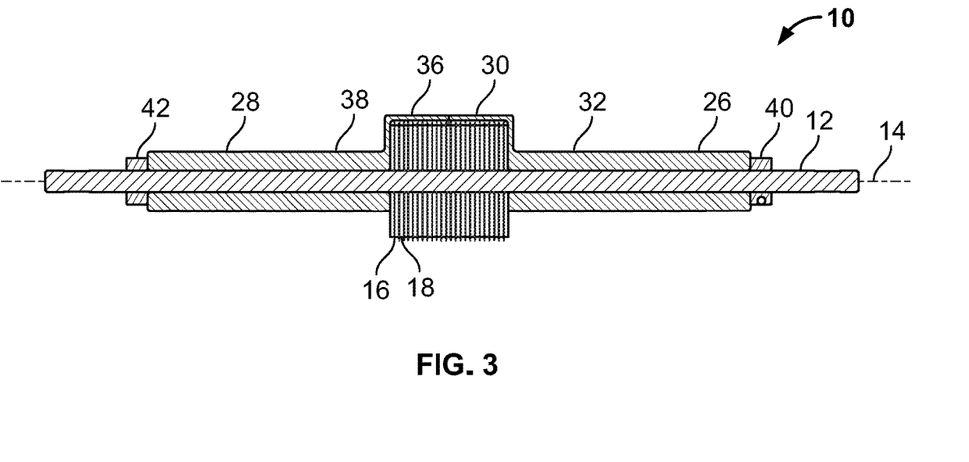
FIG. 3 is a cross-sectional plan view of the assembled rotary cutter of FIGS. 1 and 2, taken along the line A-A of FIG. 2 and looking in the direction of the arrows.

With reference generally to FIGS. 1-9, one possible configuration of the cutting device is a rotary cutter 10 having an elongated shaft, such as cylindrical shaft 12, which lies along a longitudinal rotational axis 14 (see FIGS. 1 and 3). As most clearly shown in FIGS. 3, 4 and 5, a plurality of cutting blades, such as circular cutting blades 16, and a plurality of spacer elements, such as spacer disks 18, are alternately disposed side-by-side on the shaft 12. In this rotary cutter embodiment 10, the circular cutting blades 16 and the spacer disks 18 are rotatably disposed on the cylindrical shaft 12. More particularly, there is a spacer disk 18 positioned in between each pair of adjacent circular cutting blades 16 to separate the circular cutting blades 16 by a distance that is about equal to the desired length or width of the membranous tissue fragments to be produced. In use, as will be described below, the circular cutting blades 16 rotate about the longitudinal rotational axis 14 of the rotary cutter 10.

Figure 6A:
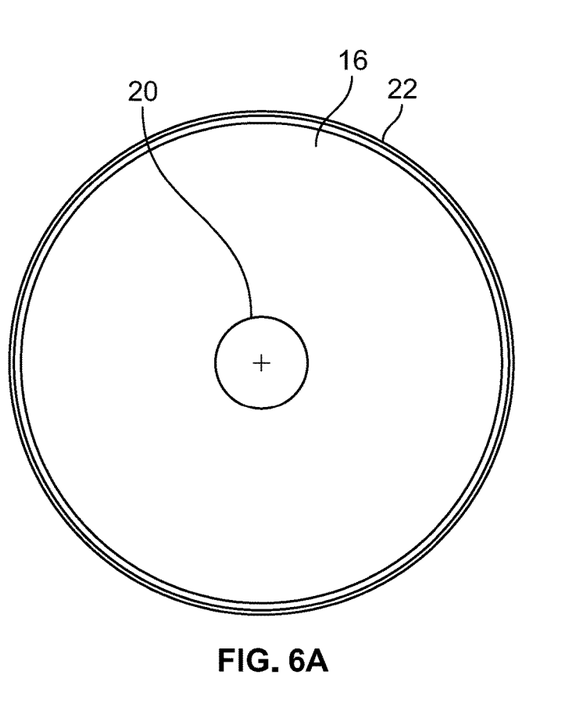
FIG. 6A is a top plan view of a circular cutting blade.
Figures 6B, 6C:
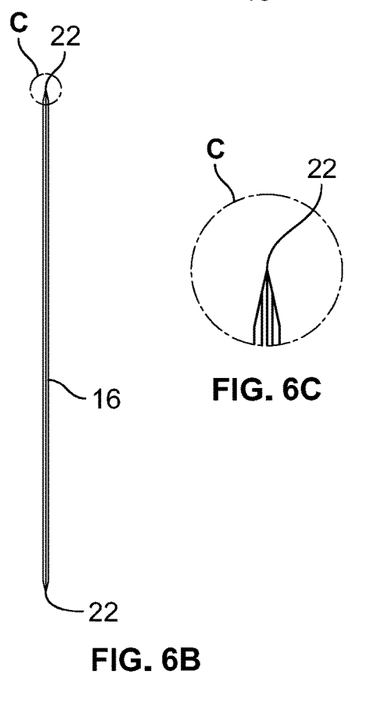
FIG. 6B is a side or edge view of the circular cutting blade of FIG. 6A.
FIG. 6C is an enlarged portion from the circle C of the side view of the circular cutting blade shown in FIG. 6B, showing the tapered cutting edge.

The circular cutting blades 16 have the same dimensions (i.e., size and shape) as one another, including diameter. As shown in FIG. 6A which shows a single circular cutting blade 16, each circular cutting blade 16 includes a centrally positioned blade opening 20 which is sized and shaped to rotatably receive the cylindrical shaft 12 therethrough. FIG. 6B shows an edge view of one circular cutting blade 16 and the tapered cutting edge 22 is visible. The tapered cutting edge 22, enclosed in circle C of FIG. 6B, is shown enlarged in FIG. 6C. This tapered cutting edge 22 extends around the entire circumference of the circular cutting blade 16 and is uniform along its entire length. The circular cutting blades 16 may, for example, be made of stainless steel, or any other material that can maintain its shape and the integrity of the tapered cutting edge 22 during use of the rotary cutter 10.

In embodiments where the cutting device 10 has cutting blades which are not circular, the blade opening may be sized and shaped to receive the elongated shaft without rotation. Additionally, rather than having a diameter, each cutting blade may have a first distance between the blade opening and the tapered cutting edge where the first distance is the same for all cutting blades.

Figure 7A:
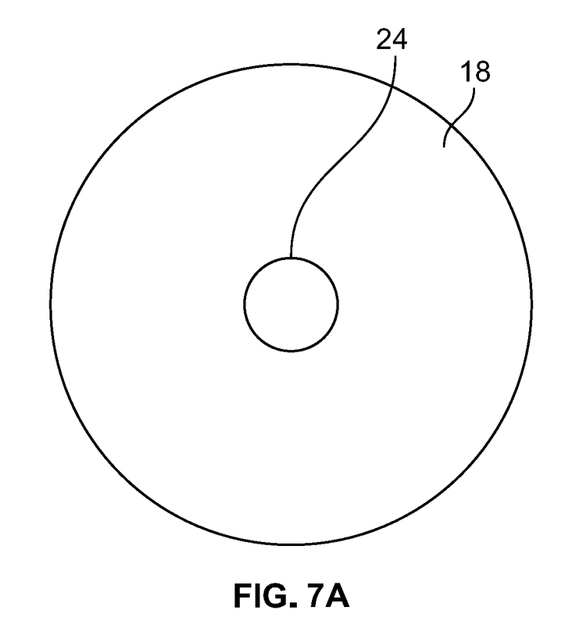
FIG. 7A is a top plan view of a spacer disk.
Figure 7B:
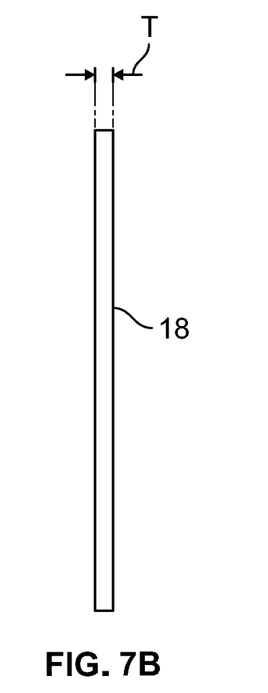
FIG. 7B is a side or edge view of the spacer disk of FIG. 7A.

The spacer disks 18 have the same dimensions as one another, including their thicknesses. As shown in FIG. 7A which shows a single spacer disk 18, each spacer disk 18 also includes a centrally positioned spacer opening 24 which is sized and shaped to rotatably receive the cylindrical shaft 12 therethrough. The thicknesses T of the spacer disks 18 (shown in FIG. 7B) are the same for all spacer disks 18 of a given rotary cutter 10 so that relatively uniformly sized membranous tissue fragments are produced. As mentioned above, the thickness T of each spacer disk 18 is sized to be about equal to the desired width or length of the membranous tissue fragments to be produced. Furthermore, the diameter of each spacer disk 18 is slightly less than the diameter of the circular cutting blades 16 so that the tapered cutting edges 22 of the circular cutting blades 16 extend beyond the spacer disks 18 to engage with and cut entirely through the membranous tissue, without obstruction or interference by the edge of the spacer disk. The spacer disks 18 may, for example, be made of stainless steel, or any other material that can maintain its shape without deformation during use of the rotary cutter 10.

In embodiments where the cutting device 10 is not rotary and, therefore, has spacer elements which are not disks, the spacer openings may each be sized and shaped to receive the elongated shaft therethrough, with or without rotation. Additionally, rather than having a diameter, each spacer element will have a tissue-facing edge which is proximate to the membranous tissue being cut during operation of the cutting device, as well as a second distance between the spacer opening and the tissue-facing edge. In such embodiments, the second distance is the same for all spacer elements and is less than the second distance of each of the cutting blades, so that the tapered cutting edges of the cutting blades extend beyond the tissue-facing edges of the spacer elements and engage with and cut entirely through the membranous tissue, without obstruction or interference by the tissue-facing edge of the spacer disk.

In embodiments where the cutting device 10 is not rotary, the first and second distances must be measured based on consistent reference points. In other words, the first distance of each cutting blade is the shortest distance between the blade opening and the cutting edge and second distance of each spacer element is the shortest distance between the spacer opening and the tissue-facing edge. Furthermore, the first distance of a cutting blade may be measured from the cutting edge to the center of the blade opening, but then the second distance of a spacer element must also be measured from the tissue-facing edge to the center of the spacer opening. Similarly, the first distance of a cutting blade may be measured from the cutting edge to the nearest edge of the blade opening, but then the second distance of a spacer element must also be measured from the tissue-facing edge to the nearest edge of the spacer opening.

For example, in an exemplary embodiment of the rotary cutting device 10, the circular cutting blades 16 are each about 45.0 mm in diameter and about 0.3 mm thick, while the spacer disks 18 are each about 42.0 mm in diameter and about 1.5 mm thick. This exemplary configuration would result in generally square shaped membranous tissue fragments having a width of about 2 mm and a length of about 2 mm, when the second cut is made at about 90 degrees to the first cut.

The rotary cutter 10 also includes first and second (e.g., right and left) guard handles 26, 28. A right guard handle 26 is shown separately in FIGS. 8 and 9. The left guard handle 28 is not shown separately but can be seen in FIGS. 1, 3, 4 and 5 and its configuration is a mirror image of the right guard handle 26. Thus, the left guard handle 28 has comparable features as those described next for the right guard handle 26. The right and left guard handles 26, 28 may be made of poly ether ether ketone (PEEK) polymer, or any other material capable of maintaining its shape without deformation during use of the rotary cutter 10. In some embodiments, the cutting device may include separate handle and guard elements. In the exemplary embodiment shown in FIGS. 1-9, these elements are combined and present as two mirror image guard handles 26, 28 as described in detail below.

Figure 5:
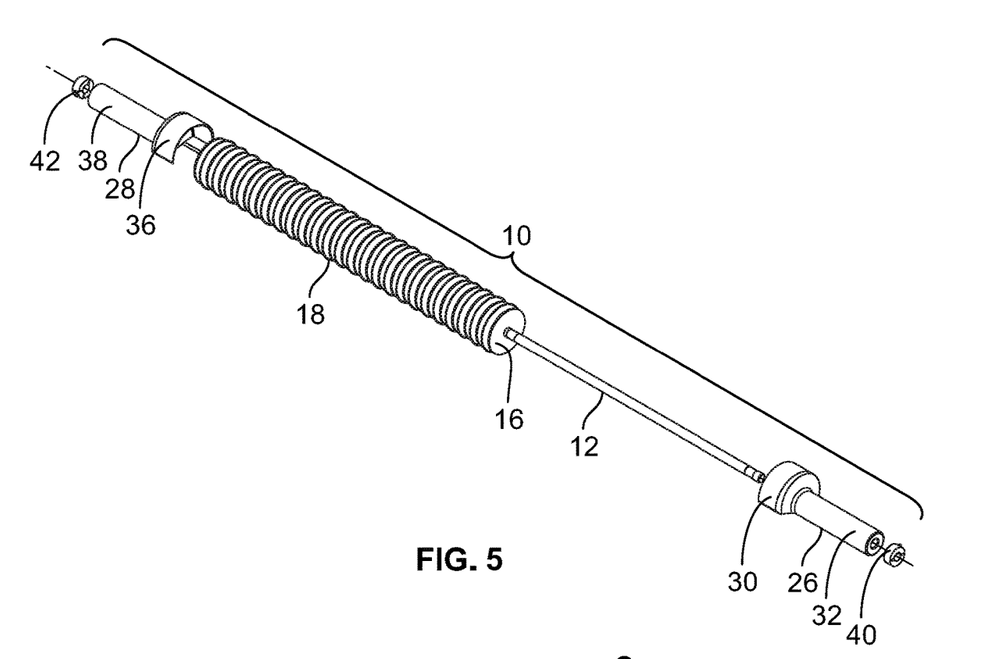
FIG. 5 is an exploded perspective view of the assembled rotary cutter of FIG. 1.
Figure 8:
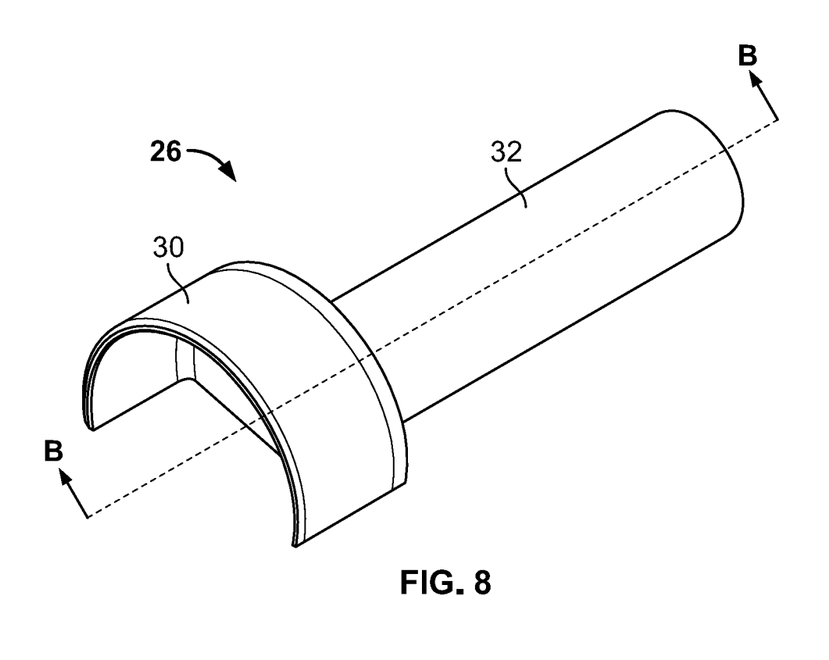
FIG. 8 is a perspective view of a right guard handle of the rotary cutter, of which the left guard handle is a mirror image.
Figure 9:
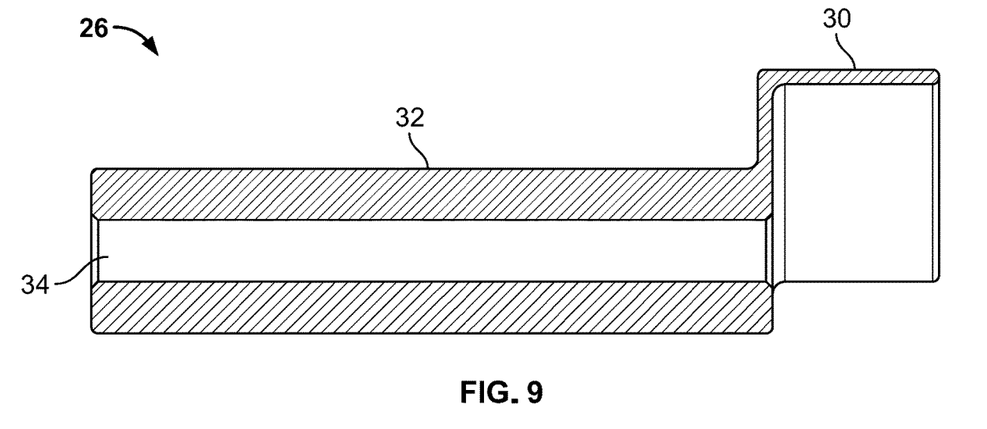
FIG. 9 is a cross-sectional plan view of the right guard handle of FIG. 8, taken along line B-B and looking in the direction of the arrows.

With reference to FIGS. 8 and 9, the right guard handle 26 has a guard portion 30 and a handle portion 32. The guard portion 30 is sized and shaped to cover a portion of the circular cutting blades 16 and spacer disks 18 without impeding their rotation (see, e.g., FIGS. 1 and 2). The exterior surface of the handle portion 32 is sized and shaped to fit into a user's hand for operation of the rotary cutter 10. The right guard handle 26 also has an arcuate bore 34, which is visible only in FIG. 9 and extends through the handle portion 32 for rotatably receiving at least a portion of the cylindrical shaft 12 therein. The left guard handle 28 also has a guard portion 36, a handle portion 38, and an arcute bore (not shown). As can be seen in FIGS. 1, 3 and 5, the right and left guard handles 26, 28 are assembled with the shaft 12, circular cutting blades 16 and spacer disks 18 such that the guard portions 30, 36 align with one another and cover a portion of the circular cutting blades 16 and spacer disks 18. The handle portions 32, 38 are rotatably fit over the shaft 12 on either side of the circular cutting blades 16 and spacer disks 18.

Figure 4:
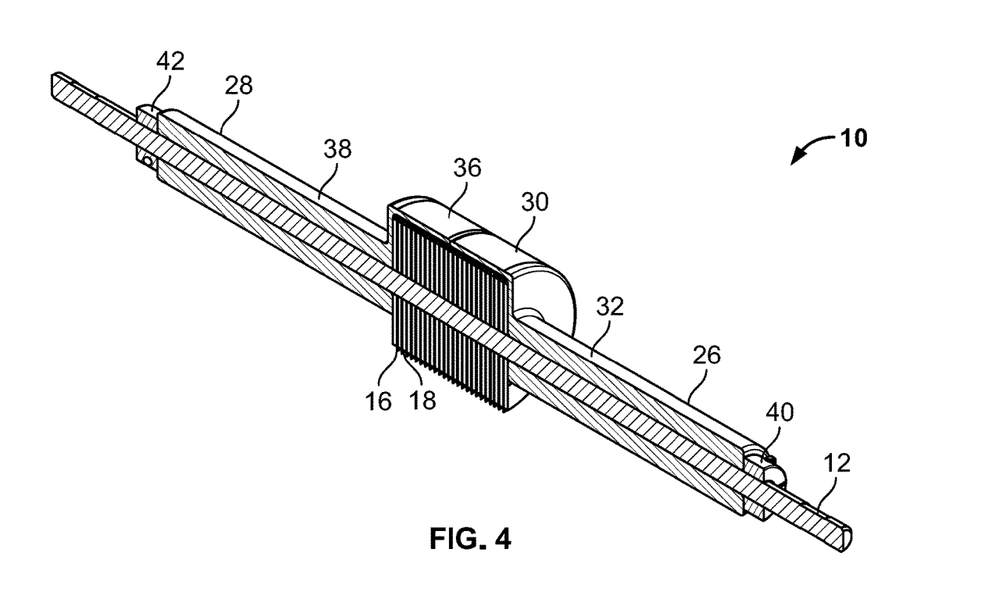
FIG. 4 is a cross-sectional perspective view of the assembled rotary cutter of FIGS. 1 and 2, taken along the line A-A of FIG. 2 and looking in the direction of the arrows.

As shown in FIGS. 1, 3 and 4, the guard portions 30, 36 of the right and left guard handles 26, 28 align with one another so that a portion (i.e., approximately half) of the assembled circular cutting blades 16 and spacer disks 18 are covered. It is the aligned guard portions 30, 36 that are on top and face the user when the rotary cutter 10 is in operation. The aligned guard portions 30, 36 protect the user from injury by the circular cutting blades 16 during handling and use of the rotary cutter 10. The aligned guard portions 30, 36 also retain membranous tissue fragments that may separate and fly up from the others and protects the user from contact with such separated membranous tissue fragments (not shown). The handle portions 32, 38 provide places for the user's hands to hold and operate the rotary cutter 10. First and second (e.g., right and left) collar clamps 40, 42 are provided (see FIGS. 1, 3, 4 and 5), each of which has an opening for receiving the shaft 12 therethrough in a secure manner so that the right and left guard handles 26, 28 are retained on the shaft 12 and remain rotatable.

As already mentioned, alternative configurations for the cutting device are possible. For example, without limitation, the cutting device may have stationary linear cutting blades (i.e., not circular and not rotatable, as mentioned above) which are spaced apart with stationary linear spacer elements (i.e., not disks and not rotatable, as mentioned above). Such an alternate embodiment could, for example, have an elongated shaft that is not cylindrical, but the blade and spacer openings would still be sized, shaped and positioned to align and receive the elongated shaft therethrough. Each of the plurality of cutting blades and each of the plurality of spacer elements would be disposed on the elongated shaft, in side-by-side and alternating arrangement with one another, such that a respective one of the plurality of spacer elements is still positioned between each respective pair of adjacent cutting blades and such that adjacent cutting blades are evenly spaced apart by a distance which is equal to the thickness of the spacer elements.

Each cutting device may have alphanumeric indicia on one or more components thereof to identify and differentiate different devices and components from one another. A particular cutting device or portion of the device such as the cutting blades and spacer disks may be discarded after use to cut all suitable areas of a single processed membranous tissue. This enhances maintenance of a sterile production process and prevents possible cross-contamination between membranous tissues that are used to produce the tissue forms comprising relatively uniformly sized and shaped membranous tissue fragments described and contemplated herein.

Pre-Cutting Preparation of Suitable Membranous Tissue

The cutting device described herein produces tissue forms comprising membranous tissue fragments from any membranous tissue, which includes any tissue that is capable of being laid flat or placed in a planar configuration for processing, even though the tissue may not be flat or planar in its natural or initial state. The membranous tissue may be derived from humans or other animals.

After recovery of membranous tissue from a consenting human donor or animal donor, the membranous tissue is typically subjected to several pre-cutting processes prior to being in condition for application of the cutting device described and contemplated herein to produce the membranous tissue fragments of the aforesaid tissue form. The pre-cutting processes often include, for example without limitation, (1) storage at sub-ambient (i.e., below about 20° C.) or freezing (i.e., below about 0° C.) temperatures, (2) physical manipulation, manual or other, to clean and remove other tissues, excess fluids, blood, and blood clots, and (3) one or more of contact, rinsing and soaking with one or more buffer solutions, salt solutions, and antibiotics.

The term "uncut processed membranous tissue" will be used hereinafter to describe the condition of the membranous tissue after performance of the desired pre-cutting processes and prior to cutting to form membranous tissue fragments. Uncut processed membranous tissue still typically includes a population of endogenous (i.e., naturally occurring) viable cells, which may or may not have already been reduced from its original size by the pre-cutting processes. Many uncut processed membraneous tissues also have an extracellular matrix, which is a supportive three-dimensional structure primarily made of various types of collagen and which may or may not have been altered from its original condition by one or more of the pre-cutting processes.

As will be understood by persons of ordinary skill in the relevant art, uncut processed membranous tissues will have varying degrees of elasticity, varying populations of cells in both type and quantity, with varying proportions of the cell populations being viable and nonviable, extracellular matrices of varying collagen content and structure, as well as varying irregular shapes with irregular edges and varying sizes, depending on many factors including, but not limited to, the type of membranous tissue from which it was derived, the particular pre-cutting processes performed, and the age of the membranous tissue.

Method

According to the method for producing a tissue form comprising membranous tissue fragments, first a membranous tissue is obtained. In some embodiments, the membranous tissue is an uncut processed membranous tissue. Optionally, any remaining liquid may be drained from the uncut processed membranous tissue. The membranous tissue is then laid flat on a cutting surface, such as a cutting board or other planar surface capable of withstanding pressure from cutting blades of the cutting device. In some embodiments, the cutting board is made of a material which reduces or avoids damage and deterioration to the cutting blades of the cutting device. In some embodiments, the cutting board is made of a material that allows the cutting blades to press slightly (i.e., less than 1 millimeter) into the surface of the cutting board which may compensate for slight (i.e., less than 1 millimeter) differences between the diameters of different cutting blades. Small cuts or slits may be made in the membranous tissue to ensure that it lies substantially flat on the planar surface, i.e., without wrinkles or folds and without air between the membrane and planar surface. Optionally, the upward-facing surface of the uncut processed membranous tissue may be manually blotted with wetted wipes to further remove excess liquid, which helps prevent it from sticking to the cutter via surface tension during cutting. After the uncut processed membranous tissue has been drained of excess liquid and placed flat on a cutting surface, one or more complete (e.g., no tears) areas of sufficient size are identified for cutting. There may be one or more areas of the appropriate size for applying the cutting device to produce the membranous tissue fragments. Thus, a single uncut processed membranous tissue may be subjected to multiple cutting sessions performed on different areas thereof until there are no areas large enough remaining.

Generally, the cutting device 10 is applied in a first direction to the flattened uncut processed membrane, proximate the complete area of appropriate size, to form a first cut and create strips in the membranous tissue. The cutting device 10 is then applied in a second direction, which is different from the first direction, to cut across the strips formed by the first cut, thereby producing relatively uniformly sized, generally quadrilaterally shaped membranous tissue fragments. In some embodiments, the second direction is rotationally between about 15 degrees and about 165 degrees from the first direction, such as for example without limitation, about 90 degrees.

More particularly, when the rotary cutter embodiment 10 is being used, it is grasped by the right and left handle portions 32, 38 of the right and left guard handles 26, 28 and aligned with one side of an area to be cut. The rotary cutter 10 is then pressed downward onto the flattened uncut processed membranous tissue so that the circular cutting blades 16 contact and cut entirely through the membranous tissue. The rotary cutter 10 is then moved horizontally across the area to be cut with pressure exerted downward and forward, to make a first cut in a first direction, effectively creating strips in the membranous tissue. It is most efficient to move the rotary cutter 10 a horizontal distance that is about the same as the total width of all the assembled circular cutting blades 16, for reasons which will become apparent. The rotary cutter 10 is then lifted clear of the membranous tissue. The membranous tissue is then rotated from about 15 to about 165 degrees, such as from about 80 to about 100 degrees, or such as about 90 degrees, and the rotary cutter 10 is aligned with an adjacent side of the area to be cut. It is most efficient if the length of the adjacent side is the same as the width of the assembled circular cutting blades 16 and spacer disks 18. The rotary cutter 10 is then pressed downward onto the membranous tissue so that the circular cutting blades 16 again contact and cut entirely through the membranous tissue. The rotary cutter 10 is then moved horizontally across the area to the cut with pressure exerted downward and forward, to make a second cut in a second direction that is rotationally from about 15 to about 165 degrees, depending on how far the membranous tissue was rotated in between cuts. The rotary cutter 10 is moved horizontally for the second cut to a distance that cuts across all strips created by the first cut. Where more than one area of the membranous tissue is to be cut, the rotary cutter 10 is preferably operated to cut the membranus tissue in both the first and second directions, prior to moving the membranous tissue to prepare for cutting the next area.

By the foregoing method, membranous tissue fragments are produced having relatively uniform size and quadrilateral shape and which may contain viable cells and mostly intact extracellular matrix. In some embodiments, each fragment is a square having a width of about 2 mm and a length of about 2 mm. Other sizes and shapes are, of course, possible and contemplated. It is desired for as many of the fragments to be as uniform as possible in size and shape, but it is not necessary or expected that each and every fragment with have exactly the same size or exactly the same shape as all the others in the population of fragments produced using the cutting device. Using the cutting device, the majority of the fragments will have the same size and the same shape, but there may also be a small percentage of the fragments that are not exactly the same size or the same shape, such as for example, some fragments may not be perfect quadrilaterals or their lengths and widths may be slightly larger or smaller than the majority of the other fragments in a population.

For an alternative embodiment as mentioned above where the cutting device is not rotary and, instead, has stationary linear cutting blades and spacer elements, a method of operation could, for example, involve positioning the cutting blades in contact with a flat uncut processed membranous tissue and pressing downward with sufficient force to cut through the entire thickness of the membranous tissue. This will form a series of cuts and strips in the membranous tissue oriented in a first direction. The membranous tissue could then be rotated anywhere between about 15 degrees and 165 degrees from the first direction, and the cutting blades again placed in contact with the membranus tissue, and the cutting device pressed downward with sufficient force to cut through the entire thickness of the membranous tissue and make a series of cuts crosswise to the first series of cuts, thereby forming membranous tissue fragments of relatively uniform size and shape. In a further alternative embodiment, where the cutting device has stationary cutting blades and the uncut unprocessed membranous tissue is mounted on a cutting board that is moveable between positions which enable cutting the membranous tissue in a first direction and in a second direction which is different from the first direction.

Resulting Tissue Form Comprising Membranous Tissue Fragments

The tissue form produced by the foregoing method using the cutting device 10 described herein comprises membranous tissue fragments each having, for example without limitation, quadrilateral, circular, polygonal, or irregular shapes. The thickness of each tissue fragment is generally the same as the thickness of the membranous tissue or tissues from which it is derived.

The tissue form comprises membranous tissue fragments each having a thickness that is the about the same thickness of the membranous tissue or tissues from which they were derived. Additionally, in some embodiments, each tissue fragment has a generally quadrilateral shape with an average length of about 0.5 to about 9 mm and an average width of about 0.5 to about 9 mm. Accordingly, in some embodiments, the tissue form will comprise tissue fragments that are squares as small as about 0.5 mm in length and about 0.5 mm in width, or squares as large as about 9 mm in length or about 9 mm in width, or they may be rectangles or parallelograms having dimensions anywhere in between.

The membranous tissue fragments may be combined with a liquid, such as cryopreservation solution, saline or buffer solution, then packaged and stored until use. Where the liquid is cryopreservation solution, the tissue form may be cryopreserved, in some embodiments, after packaging. Suitable cryopreservavtion solutions include, for example without limitation, 10% by volume dimethyl sulfoxide (DMSO), Dulbecco's Modified Eagles Media (DMEM), and Fetal Bovine Serum and DMSO in a 60/30/10 percent by volume ratio. A tissue form comprising membranous tissue fragments produced as described herein and a liquid, such as cryopreservation fluid, saline or buffer solution, is flowable to which means the mixture will easily pass through a 14 gauge needle or luer-slip tip syringe. The membranous tissue fragments may contain viable endogenous cells. The term "endogenous" as used herein means naturally occurring or present in tissue after recovery and before processing. The term "viable" as used herein refers to having the ability to grow, expand, or develop; capable of living and/or is metabolically active. The tissue form may also contain intact extracellular matrix.

It will be understood that the embodiments described herein are merely exemplary and that a person of ordinary skill in the art may make many variations and modifications not mentioned herein without departing from the spirit and scope of the invention. All such variations and modifications are intended to be included within the scope of the invention, as defined by the appended claims.

The invention claimed is:

1. A rotary cutting device for producing a tissue form comprising uniformly sized and shaped membranous tissue fragments derived from tissue, the rotary cutting device comprising:

a plurality of cutting blades, each of which is circular and has a size, a tapered cutting edge, a blade opening therethrough having a center, and a first distance between the center of the blade opening and the tapered cutting edge, wherein the size, and the first distance are, respectively, the same for each of the circular cutting blades, and the blade openings are each centrally positioned on their respective circular cutting blade;

a plurality of spacer disks, each of which is circular and has a size, a thickness, a tissue facing edge, a spacer opening therethrough having a center, and a second distance between the center of the spacer opening and the tissue facing edge, wherein the size, the thickness and the second distance are, respectively, the same for each of the plurality of spacer disks, and the spacer openings are each centrally positioned on their respective spacer disk;

a cylindrical shaft having a longitudinal axis and on which the circular cutting blades and the plurality of spacer disks are removably disposed and rotatably supported and aligned, in side-by-side and alternating arrangement with one another, such that adjacent circular cutting blades are evenly spaced apart by a third distance which is equal to the thickness of each of the plurality of spacer disks positioned therebetween, and wherein a first portion of the cylindrical shaft extends from a first side of the side-by-side and alternating circular cutting blades and plurality of spacer disks, along the longitudinal axis, and a second portion of the cylindrical shaft extends from a second opposite side of the side-by-side and alternating circular cutting blades and plurality of spacer disks, along the longitudinal axis;

a right guard handle which extends along the longitudinal axis of the cylindrical shaft and has: a right guard portion which is sized and shaped to cover a portion of the side-by-side and alternating circular cutting blades and plurality of spacer disks disposed on the cylindrical shaft without impeding their rotation, and a right handle portion positioned to be held in a user's right hand during operation of the rotary cutting device and an elongated bore which extends through the right handle portion and in which the first portion of the cylindrical shaft is rotatably received; and a left guard handle which extends along the longitudinal axis of the cylindrical shaft, is a mirror image of the right guard handle and has: a left guard portion which is sized and shaped to cover a portion of the side-by-side and alternating circular cutting blades and plurality of spacer disks disposed on the cylindrical shaft without impeding their rotation, and a left handle portion positioned to be held in a user's left hand during operation of the rotary cutting device and an elongated bore which extends through the left handle portion and in which the second portion of the cylindrical shaft is rotatably received;

wherein the right guard portion and the left guard portion are configured to be proximate and facing a user during operation of the rotary cutting device;

wherein the blade openings and the spacer openings are all sized, shaped and positioned on their respective circular cutting blades and spacer disks such that the blade openings and spacer openings are aligned with one another and receive the cylindrical shaft therethrough; and wherein the second distance of each of the plurality of spacer disks is less than the first distance of each of the circular cutting blades so that the tapered cutting edges of the circular cutting blades will cut entirely through a membranous tissue without obstruction or interference from the tissue facing edges of the plurality of spacer disks when the rotary cutting device is operated.

2. The rotary cutting device of claim 1, wherein each circular cutting blade has a blade circumference and each tapered cutting edge extends around the respective entire blade circumference and is uniform along its entire length.

3. The rotary cutting device of claim 1, wherein each circular cutting blade has a blade diameter, the blade diameters are all equal to one another, and each first distance is equal to one half the blade diameter, wherein each spacer disk has a spacer circumference and a spacer diameter, the tissue facing edge of each spacer disk is positioned on its respective circumference, the spacer diameters are all equal to one another, and each second distance is equal to one half the spacer diameter, and wherein each spacer diameter is less than each blade diameter such that the tapered cutting edges of the circular cutting blades will cut entirely through the membranous tissue without obstruction or interference from the tissue facing edges of the plurality of spacer disks when the rotary cutting device is operated.

4. The rotary cutting device of claim 3, wherein each circular cutting blade has a thickness of about 0.3 millimeter, the blade diameter of each circular cutting blade is about 45.0 millimeters, the spacer diameter of each spacer disk is about 42.0 millimeters, the thickness of each spacer disk is about 1.5 millimeters, and each of the membranous tissue fragments of the tissue form produced using the rotary cutting device has a width of about 2 millimeters and a length of about 2 millimeters.

5. The cutting device of claim 1, wherein the right and left guard handles are assembled with the cylindrical shaft, the circular cutting blades, and the plurality of spacer disks, wherein the left and right guard portions align with one another and together cover a portion of the circular cutting blades and the plurality of spacer disks, and the right and left handle portions rotatably fit over the cylindrical shaft, on either side of the assembled circular cutting blades and the plurality of spacer disks.

6. A method for producing a tissue form comprising membranous tissue fragments from a membranous tissue using the rotary cutting device of claim 1, the method comprising:
    providing a membranous tissue;
    positioning the rotary cutting device proximate to the membranous tissue;
    applying the rotary cutting device in a first direction to the membranous tissue to form a first cut entirely through the membranous tissue and thereby create at least one strip in the membranous tissue;
    repositioning the rotary cutting device, the membranous tissue, or both; and
    applying the rotary cutting device in a second direction, which is different from the first direction, to form a second cut entirely through the membranous tissue and across the at least one strip which was formed by the step of applying the rotary cutting device in the first direction, thereby producing uniformly sized and shaped membranous tissue fragments.

7. The method of claim 6, wherein the second direction is rotationally between about 15 degrees and about 165 degrees from the first direction.

8. The method of claim 7, wherein the second direction is rotationally about 90 degrees from the first direction.

9. The method of claim 6, wherein the step of applying the rotary cutting device in the first direction to the membranous tissue includes pressing the rotary cutting device downward onto the membranous tissue so that the circular cutting blades contact and cut entirely through the membranous tissue, and moving the rotary cutting device horizontally across the membranous tissue with pressure exerted downward and forward in the first direction.

10. The method of claim 6, wherein the step of applying the rotary cutting device in the second direction to the membranous tissue includes pressing the rotary cutting device downward onto the membranous tissue so that the circular cutting blades contact and cut entirely through the membranous tissue, and moving the rotary cutting device horizontally across the membranous tissue with pressure exerted downward and forward in the second direction.

11. The method of claim 6, wherein the circular cutting blades of the rotary cutting device have a total width and the step of applying the rotary cutting device in the first direction includes moving the rotary cutting device in the first direction for a horizontal distance that is about equal to the total width of the circular cutting blades.

12. The method of claim 11, wherein the step of applying the rotary cutting device in the second direction includes moving the rotary cutting device in the first direction for a horizontal distance that cuts across all of the at least one strip created by the first cut.

13. The method of claim 6, wherein the step of providing the membranous tissue includes identifying an area of the membranous tissue having appropriate size to apply the rotary cutting device in both the first and second directions; and performing the steps of applying the rotary cutting device to the membranous tissue in the first and second directions include applying the rotary cutting device to the area of the membranous tissue having appropriate size.

* * * * *